United States Patent [19]

Sasajima et al.

[11] 4,235,914
[45] Nov. 25, 1980

[54] PSYCHOTROPIC γ-(HETEROCYCLIC SUBSTITUTED) BUTYROPHENONES

[75] Inventors: Kikuo Sasajima, Toyonaka; Keiichi Ono, Nishinomiya; Hisao Yamamoto, Kobe, all of Japan

[73] Assignee: Sumitomo Chemical Company, Limited, Osaka, Japan

[21] Appl. No.: 952,104

[22] Filed: Oct. 17, 1978

Related U.S. Application Data

[63] Continuation of Ser. No. 663,763, Mar. 4, 1976, abandoned.

[30] Foreign Application Priority Data

Mar. 5, 1975 [JP] Japan .................................. 50/27489
Nov. 18, 1975 [JP] Japan .................................. 50/138836

[51] Int. Cl.$^3$ .................. A61K 31/445; C07D 211/52; C07D 235/26; C07D 471/10
[52] U.S. Cl. .............................. 424/267; 260/326.5 J; 424/248.58; 424/250; 424/263; 424/274; 424/330; 544/173; 544/392; 544/398; 544/399; 544/401; 544/402; 546/20; 546/199; 546/216; 546/217; 546/225; 546/271; 564/342
[58] Field of Search ................. 546/199, 20, 216, 217, 546/271; 544/392; 424/250, 267

[56] References Cited

U.S. PATENT DOCUMENTS

| | | | |
|---|---|---|---|
| 3,799,932 | 3/1974 | Yamamoto et al. | 546/237 |
| 3,979,390 | 9/1976 | Sasajima et al. | 544/392 |

FOREIGN PATENT DOCUMENTS 47-18878 9/1972 Japan ...................................... 546/217

OTHER PUBLICATIONS

Janssen, P., *Int. J. Neuropharmacol.,* 1962, 1, 145–148.

*Primary Examiner*—Henry R. Jiles
*Assistant Examiner*—Richard A. Schwartz
*Attorney, Agent, or Firm*—Birch, Stewart, Kolasch & Birch

[57] ABSTRACT

Butyrophenone compounds having excellent psychotropic activity and represented by the formula:

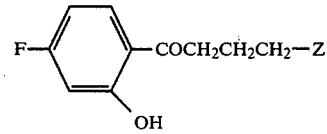

wherein Z is defined hereinbelow.

6 Claims, No Drawings

PSYCHOTROPIC γ-(HETEROCYCLIC SUBSTITUTED) BUTYROPHENONES

This application is a continuation of copending application Ser. No. 663,763, filed on Mar. 4, 1976, now abandoned.

The present invention relates to novel butyrophenone compounds having a central nervous system depressing activity, to a pharmaceutical composition containing them, and to a process for production thereof.

The said novel butyrophenone compounds are representable by the formula:

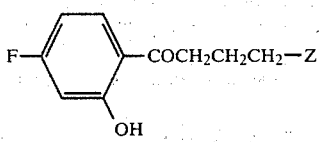

[I]

wherein Z is a group of either one of the formulae:

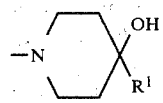

wherein $R^1$ is a benzyl group, a 2,4-dichlorobenzyl group, a 4-chlorobenzyl group, a 3,4-dichlorobenzyl group, a 3-trifluoromethylphenyl group, a 3-trifluoromethyl-4-chlorophenyl group or a 3,4-dichlorophenyl group;

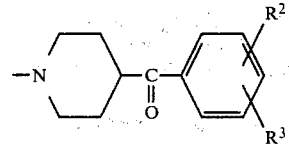

wherein $R^2$ and $R^3$ are each a hydrogen atom, a halogen atom, a trifluoromethyl group, a lower alkyl group or a lower alkoxy group;

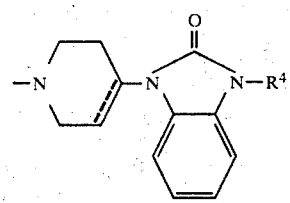

wherein the dotted line indicates the optional presence of an additional single bond linkage and $R^4$ is a hydrogen atom or a lower alkyl group;

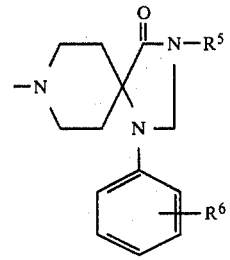

wherein $R^5$ is a hydrogen atom or a lower alkyl group and $R^6$ is a hydrogen atom or a halogen atom;

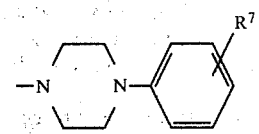

wherein $R^7$ is a hydrogen atom or a lower alkoxy group;

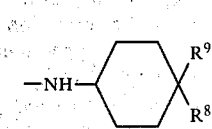

wherein $R^8$ and $R^9$ are each a hydrogen atom, a lower alkyl group or a phenyl group optionally substituted with one substituent selected from the group consisting of halogen, lower alkyl and lower alkoxy;

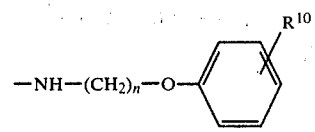

wherein $R^{10}$ is a hydrogen atom, a lower alkyl group, a lower alkoxy group or a trifluoromethyl group and n is an integer of from 1 to 4;

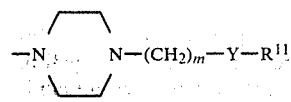

wherein $R^{11}$ is a hydrogen atom, a lower alkyl group or a phenyl group optionally substituted with one or two substituents selected from the group consisting of halogen, lower alkyl, lower alkoxy and trifluoromethyl, Y is an oxygen atom, a sulfur atom, a carbonyl group or a group of either one of the formulae:

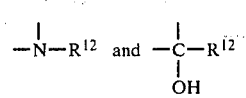

wherein $R^{12}$ is a hydrogen atom, a lower alkyl group or a phenyl group optionally substituted with one or two substituents selected from the group consisting of halogen, lower alkyl, lower alkoxy and trifluoromethyl and m is an integer of from 1 to 4;

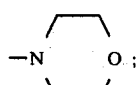

and

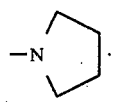

In the significances as defined above, "lower alkyl" and "lower alkoxy" include one to about four carbon atoms and may be straight or branched groups. Examples thereof are methyl, ethyl, n-propyl, isopropyl, n-butyl, isobutyl, t-butyl, methoxy, ethoxy, n-propoxy, isopropoxy, n-butoxy, isobutoxy and t-butoxy. The term "halogen" includes fluorine, chlorine, bromine and iodine.

Accordingly, an object of the present invention is to provide novel butyrophenone compounds [I] having a central nervous system depressing activity. Another object of this invention is to provide a pharmaceutical composition containing the butyrophenone compounds [I]. A further object of the invention is to provide a process for producing the butyrophenone compounds [I]. These and other objects will be apparent to those skilled in the art to which the present invention pertains from the foregoing and subsequent descriptions.

According to the present invention, the butyrophenone compounds [I] can be prepared by reacting a compound of the formula:

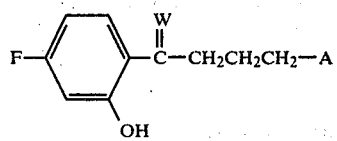  [II]

wherein A is a halogen atom (e.g. chlorine, bromine, iodine) and

is a carbonyl group or a protected carbonyl group (e.g. W is an oxygen atom, an ethylenedioxy group or an ethylenedithio group) with a compound of the formula:

  [III]

wherein Z is as defined above to give a compound of the formula:

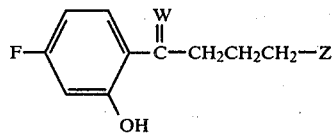  [IV]

wherein Z and W are each as defined above, optionally followed by hydrolysis of the latter.

The compound [II] can be prepared by reacting m-fluorophenol with a compound of the formula:

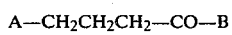  [V]

wherein A is as defined above and B is a halogen atom or a hydroxyl group, optionally followed by protection of the carbonyl group.

The condensation reaction of the compound [II] with the compound [III] in the free base or salt form is usually carried out in an inert solvent such as an aromatic hydrocarbon (e.g. benzene, toluene, xylene), an amide (e.g. dimethylformamide, dimethylacetamide), an ether (e.g. dioxane, tetrahydrofuran), an alcohol (e.g. ethanol, n-propanol, butanol, amyl alcohol), an alkanone (e.g. acetone, butanone, methylisobutylketone) or dimethylsulfoxide at a temperature within the range of room temperature to the boiling point of the solvent. Preferably, there may be used a basic substance such as an alkali carbonate (e.g. sodium carbonate, potassium carbonate), an alkali hydrogen carbonate (e.g. sodium hydrogen carbonate, potassium hydrogen carbonate), an alkali hydroxide (e.g. sodium hydroxide, potassium hydroxide) or an organic amine (e.g. pyridine, triethylamine) as an acid binding agent. There may be also used a small amount of a reaction accelerating agent such as potassium iodide.

The hydrolysis can be carried out by a conventional acid hydrolyzing procedure. For instance, it can be accomplished by treating the compound [IV] with an acidic substance such as a mineral acid (e.g. hydrochloric acid, sulfuric acid, phosphoric acid), an organic acid (e.g. oxalic acid, tartaric acid) or an acidic ion exchange resin in water or an alkanol (e.g. methanol, ethanol, propanol), usually under a mild condition, e.g. at room temperature. Further, it may be accelerated by elevation of the temperature.

The reaction of m-fluorophenol with the compound [V] is usually carried out in the presence of a Lewis acid (e.g. anhydrous aluminum chloride, stannic chloride, boron trifluoride) at a temperature within a range of 50° to 250° C. without a solvent. Further, it is possible to carry out the reaction in an inert solvent such as carbon disulfide, dichloromethane, nitromethane or nitrobenzene. In most cases, the reaction can be accelerated at elevated temperatures, preferably from 100° to 200° C.

The protection of a carbonyl group may be carried out by a conventional procedure.

Specific examples of the butyrophenone compound [I] are as follows:

γ-(4-Oxo-1-phenyl-1,3,8-triazaspiro[4,5]decan-8-yl)-2-hydroxy-4-fluorobutyrophenone;

γ-[4-(2-Oxo-1-benzimidazolinyl)piperidin-1-yl]-2-hydroxy-4-fluorobutyrophenone;

γ-[4-(2-Oxo-1-benzimidazolinyl)-1,2,3,6-tetrahydropyridin-1-yl]-2-hydroxy-4-fluorobutyrophenone;

γ-(4-Phenylpiperazino)-2-hydroxy-4-fluorobutyrophenone;

γ-[4-(2-Methoxyphenyl)piperazino]-2-hydroxy-4-fluorobutyrophenone;

γ-(4-Benzyl-4-hydroxypiperidino)-2-hydroxy-4-fluorobutyrophenone;

γ-[4-(4-Chlorobenzyl)-4-hydroxypiperidino]-2-hydroxy-4-fluorobutyrophenone;

γ-Morpholino-2-hydroxy-4-fluorobutyrophenone;

γ-Pyrrolidino-2-hydroxy-4-fluorobutyrophenone;

γ-(4-Benzoylpiperidino)-2-hydroxy-4-fluorobutyrophenone;

γ-[4-(4-Fluorobenzoyl)piperidino]-2-hydroxy-4-fluorobutyrophenone; γ-[4-(3-Phenoxypropyl)piperazino]-2-hydroxy-4-fluorobutyrophenone;

γ-[4-(2-Phenoxyethyl)piperazino]-2-hydroxy-4-fluorobutyrophenone;
γ-[4-(2-Diphenylaminoethyl)piperazino]-2-hydroxy-4-fluorobutyrophenone;
γ-[4-(3-Phenylthiopropyl)piperazino]-2-hydroxy-4-fluorobutyrophenone;
γ-[4-(3,3-Diphenyl-3-hydroxypropyl)piperazino]-2-hydroxy-4-fluorobutyrophenone;
γ-[4-(4-Phenyl-4-hydroxybutyl)piperazino]-2-hydroxy-4-fluorobutyrophenone;
γ-(2-Phenoxyethylamino)-2-hydroxy-4-fluorobutyrophenone;
γ-[2-(2-Methoxyphenoxy)ethylamino]-2-hydroxy-4-fluorobutyrophenone;
γ-[2-(2-Ethoxyphenoxy)ethylamino]-2-hydroxy-4-fluorobutyrophenone;
γ-Cyclohexylamino-2-hydroxy-4-fluorobutyrophenone;
γ-(4-Phenylcyclohexylamino)-2-hydroxy-4-fluorobutyrophenone;
γ-[4-(4-Fluorophenyl)cyclohexylamino]-2-hydroxy-4-fluorobutyrophenone;
γ-[4-(3-Trifluoromethylphenyl)-4-hydroxypiperidino]-2-hydroxy-4-fluorobutyrophenone;
γ-[4-(3-Trifluoromethyl-4-chlorophenyl)-4-hydroxypiperidino]-2-hydroxy-4-fluorobutyrophenone;
γ-[4-(3,4-Dichlorophenyl)-4-hydroxypiperidino]-2-hydroxy-4-fluorobutyrophenone;
γ-[4-(3,4-Dichlorobenzyl)-4-hydroxypiperidino]-2-hydroxy-4-fluorobutyrophenone, etc.

These butyrophenone compounds [I] in the free base form can be converted into their pharmaceutically acceptable salts such as acid addition salts or quaternary ammonium salts by treatment with mineral acids (e.g. hydrochloric acid, hydrobromic acid, sulfuric acid, phosphoric acid), organic acids (e.g. acetic acid, citric acid, oxalic acid, lactic acid, succinic acid, tartaric acid, cinnamic acid, ascorbic acid), alkyl halides, aralkyl halides, aromatic sulfonates or the like.

The butyrophenone compounds [I] in the free base or salt form have a variety of useful pharmacological properties, for example, central nervous system depressing activity and anti-adrenergic activity. Thus, they are useful as anti-psychotic and anti-hypertensive drugs, and can be used for treating a patient suffering from hypertension or mental disease. For instance, they exhibit an anti-apomorphine activity in rats greater than that of chlorpromazine and γ-[4-(4-chlorophenyl)-4-hydroxypiperidino]-2-hydroxy-4-fluorobutyrophenone disclosed in Belgian Pat. No. 753,472.

Among the butyrophenone compounds [I], those wherein Z is a group of either one of the formulae:

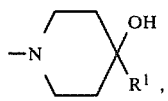

and

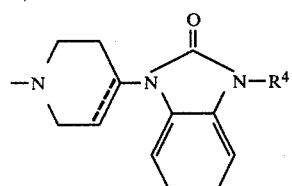

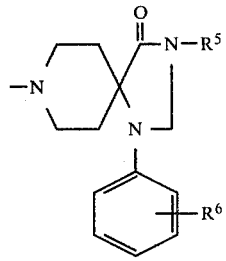

wherein $R^1$, $R^4$, $R^5$ and $R^6$ are each as defined above display particularly excellent anti-psychotic properties when evaluated by an anti-apomorphine activity test in rats.

The butyrophenone compounds [I] wherein Z is the group of the formula:

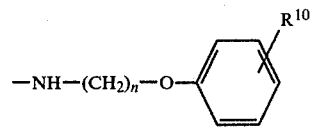

wherein $R^{10}$ and n are each as defined above show particularly therapeutically desirable alpha-adrenergic blocking properties as anti-hypertensive agents.

Each of the butyrophenone compounds [I] may be brought into a form suitable for administration according to a method known per se.

For the preparation of pharmaceutical compositions, they may be mixed with carriers or diluents such as water, sesame oil, calcium phosphate, starch, talcum, casein, magnesium stearate, methyl cellulose, polyglycols, tragacanth and the like, sometimes together with stabilizers and/or emulsifying agents.

The resulting mixture may be processed in accordance with usual procedures to give tablets, capsules, pills, ampoules and the like. The usual oral dosage is 1–200 mg daily.

Practical and preferred embodiments of the present invention are illustratively shown in the following examples, which are not intended to limit the scope of the invention thereto.

EXAMPLE 1

A mixture of 53 g of m-fluorophenol, 132 g of γ-chlorobutyryl chloride and 270 g of boron trifluoride etherate was refluxed for 5.5 hours. The resulting mixture was poured into ice water and extracted with ethyl acetate. The extract was washed successively with dilute aqueous sodium hydrogen carbonate and saturated aqueous sodium chloride, dried over anhydrous sodium sulfate and evaporated under reduced pressure. The residual oil was distilled to give γ-chloro-2-hydroxy-4-fluorobutyrophenone, B.P. 128°–131° C./1.1 mmHg.

EXAMPLE 2

A mixture of 10 g of γ-chloro-2-hydroxy-4-fluorobutyrophenone, 6.6 g of 4-(2-keto-1-benzimidazolinyl)piperidine, 2.6 g of sodium hydrogen carbonate, 0.05 g of potassium iodide and 300 ml of toluene was refluxed for 27 hours. The resulting mixture was poured into ice water and extracted with chloroform. The extract was washed with saturated aqueous sodium chloride, dried over anhydrous sodium sulfate and evaporated under reduced pressure. The residual viscous oil was chromatographed over silica gel (100–200 mesh) with ethyl acetate as an eluting agent to give γ-[4-(2-keto-1-benzimidazolinyl)piperidin-1-yl]-2-hydroxy-4-fluorobutyrophenone, M.P. 175°–181° C.

EXAMPLE 3

A mixture of 18.75 g of γ-chloro-2-hydroxy-4-fluorobutyrophenone, 5.25 g of sodium hydrogen carbonate, 15 g of 1-phenyl-1,3,8-triazaspiro[4,5]decan-4-one, 0.02 g of potassium iodide and 2 liters of toluene was refluxed for 80 hours. The resulting mixture was poured into ice water and extracted with ethyl acetate. The extract was washed with saturated aqueous sodium chloride, dried over anhydrous sodium sulfate and evaporated under reduced pressure. The residual solid was washed with diethyl ether to give γ-(4-oxo-1-phenyl-1,3,8-triazaspiro[4,5]decan-8-yl)-2-hydroxy-4-fluorobutyrophenone, M.P. 215°–220° C.

EXAMPLE 4

In the same manner as in Examples 2 and 3, the following compounds were obtained:

γ-[4-(3-Trifluoromethylphenyl)-4-hydroxypiperidino]-2-hydroxy-4-fluorobutyrophenone hydrochloride, M.P. 218°–221° C.;

γ-[4-(3-Trifluoromethyl-4-chlorophenyl)-4-hydroxypiperidino]-2-hydroxy-4-fluorobutyrophenone hydrochloride, M.P. 210°–211° C.;

γ-[4-(3,4-Dichlorophenyl)-4-hydroxypiperidino]-2-hydroxy-4-fluorobutyrophenone hydrochloride, M.P. 202°–210° C.

What is claimed is:

1. γ-[4-(3-Trifluoromethylphenyl)-4-hydroxypiperidino]-2-hydroxy-4-fluorobutyrophenone, or a pharmaceutically acceptable acid addition salt thereof.

2. γ-[4-(2-Keto-1-benzimidazolinyl)piperidin-1-yl]-2-hydroxy-4-fluorobutyrophenone, or a pharmaceutically acceptable acid addition salt thereof.

3. γ-[4-Oxo-1-phenyl-1,3,8-triazaspiro[4,5]-decan-8-yl]-2-hydroxy-4-fluorobutyrophenone, or a pharmaceutically acceptable acid addition salt thereof.

4. An antipsychotic composition comprising an effective antipsychotic amount of at least one of the compounds as claimed in any one of claims 1, 2 or 3 or a pharmaceutically acceptable salt thereof, and at least one pharmaceutically acceptable diluent or carrier.

5. A method of treating a patient suffering from mental disease which comprises administering to said patient an effective psychotropic amount of a compound according to any one of claims 1, 2 or 3.

6. The method according to claim 5, wherein from 1 to 200 mg. of said compound is administered orally to the patient daily.

* * * * *